United States Patent
Belalcazar et al.

(10) Patent No.: US 7,184,821 B2
(45) Date of Patent: Feb. 27, 2007

(54) MONITORING THORACIC FLUID CHANGES

(75) Inventors: Andres Belalcazar, St Paul, MN (US); Robert Patterson, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 375 days.

(21) Appl. No.: 10/726,949

(22) Filed: Dec. 3, 2003

(65) Prior Publication Data

US 2005/0124908 A1    Jun. 9, 2005

(51) Int. Cl.
*A61B 5/05*    (2006.01)

(52) U.S. Cl. ...................................... 600/547

(58) Field of Classification Search ................ 600/547, 600/506, 529, 536; 607/6, 17
See application file for complete search history.

(56) References Cited

U.S. PATENT DOCUMENTS

| | | | |
|---|---|---|---|
| 3,340,867 A | 9/1967 | Kubicek et al. | |
| 4,932,408 A | 6/1990 | Schaldach | |
| 5,154,170 A | 10/1992 | Bennett et al. | |
| 5,284,136 A | 2/1994 | Hauck et al. | |
| 5,438,987 A | 8/1995 | Thacker et al. | |
| 5,501,702 A | 3/1996 | Plicchi et al. | |
| 5,556,421 A | 9/1996 | Prutchi et al. | |
| 5,755,742 A * | 5/1998 | Schuelke et al. | 607/27 |
| 5,782,774 A * | 7/1998 | Shmulewitz | 600/547 |
| 5,814,076 A | 9/1998 | Brownlee | |
| 5,824,029 A | 10/1998 | Weijand et al. | |
| 5,876,353 A | 3/1999 | Riff | |
| 5,931,858 A | 8/1999 | Kadhiresan et al. | |
| 5,957,861 A | 9/1999 | Combs et al. | |
| 5,974,340 A | 10/1999 | Kadhiresan | |
| 6,070,100 A | 5/2000 | Bakels et al. | |
| 6,076,015 A | 6/2000 | Hartley et al. | |
| 6,095,987 A * | 8/2000 | Shmulewitz et al. | 600/547 |
| 6,104,949 A * | 8/2000 | Pitts Crick et al. | 600/547 |
| 6,161,042 A | 12/2000 | Hartley et al. | |
| 6,223,079 B1 | 4/2001 | Bakels et al. | |
| 6,269,264 B1 | 7/2001 | Weyant et al. | |

(Continued)

OTHER PUBLICATIONS

Bocchiardo et al., "Biventricular Pacing Optimization Using Impedance Feasibility Study," *Europace Supplements*, 2002, 3:A39, Abstract No. 54/3.

(Continued)

*Primary Examiner*—Max F. Hindenburg
*Assistant Examiner*—Michael Apanius
(74) *Attorney, Agent, or Firm*—Fish & Richardson P.C.

(57) ABSTRACT

Changes in fluid volume in a thoracic region, such as the lung, are detected by internally injecting a current through the region, detecting an induced voltage on the skin of the patient, and calculating an impedance value. A method for performing such a measurement includes injecting an electrical current between first and second internal electrodes that are implanted in the body and that are positioned such that a portion of the injected current flows through at least a portion of the region. The method also includes measuring a voltage between first and second external electrodes attached to an external surface of the skin of the body. The measured voltage is induced by the injected current. The method also includes calculating an impedance by taking the ratio of the measured voltage and the injected current, wherein the calculated impedance is related to the volume of fluid in the region.

43 Claims, 4 Drawing Sheets

U.S. PATENT DOCUMENTS

| | | | |
|---|---|---|---|
| 6,277,078 | B1 | 8/2001 | Porat et al. |
| 6,278,894 | B1 | 8/2001 | Salo et al. |
| 6,360,123 | B1 | 3/2002 | Kimchi et al. |
| 6,370,424 | B1 * | 4/2002 | Prutchi .................. 600/547 |
| 6,438,408 | B1 | 8/2002 | Mulligan et al. |
| 6,454,719 | B1 | 9/2002 | Greenhut |
| 6,473,640 | B1 * | 10/2002 | Erlebacher ............. 600/547 |
| 6,496,732 | B1 * | 12/2002 | Wallace ................. 607/24 |
| 6,512,949 | B1 | 1/2003 | Combs et al. |
| 6,595,927 | B2 * | 7/2003 | Pitts-Crick et al. ...... 600/529 |
| 2001/0020138 | A1 | 9/2001 | Ishigooka et al. |
| 2002/0002389 | A1 | 1/2002 | Bradley et al. |
| 2002/0115939 | A1 | 8/2002 | Mulligan et al. |
| 2002/0123674 | A1 | 9/2002 | Plicchi et al. |
| 2002/0143368 | A1 | 10/2002 | Bakels et al. |
| 2002/0161310 | A1 | 10/2002 | Daum |
| 2003/0023184 | A1 | 1/2003 | Pitts-Crick et al. |
| 2003/0028221 | A1 | 2/2003 | Zhu et al. |
| 2003/0078619 | A1 | 4/2003 | Bonnet et al. |
| 2003/0093125 | A1 | 5/2003 | Zhu et al. |
| 2004/0102712 | A1 | 5/2004 | Belalcazar et al. |
| 2004/0116819 | A1 * | 6/2004 | Alt ......................... 600/513 |

OTHER PUBLICATIONS

Bronzino (ed.), "Chapter 73—Bioelectric Impedance Measurements," *The Biomedical Engineering Handbook*, Second Edition, vol. 1, 2000, A CRC Handbook Published in Cooperation with IEEE Press, pp. 73-1—73-8.

Cole et al., "Correlation of Impedance Minute Ventilation with Measured Minute Ventilation in a Rate Responsive Pacemaker," *PACE*, 2001, 24:989-993.

Duru et al., "Rate Responsive Pacing Using Transthoracic Impedance Minute Ventilation Sensors: A Multicenter Study on Calibration Stability," *PACE*, 2002, 25(12):1679-1684.

Hauck, "A Minute Ventilation Sensor Derived from Intra-Thoracic Electric Impedance as a Cardiac Pacemaker Rate Modulator," A Thesis Submitted to the Faculty of the Graduate School of the University of Minnesota, Department of Electrical Engineering, Jun. 1993, 148 pgs.

Nappholtz et al., "Electrode Configurations for a Respiratory Impedance Measurement Suitable for Rate Responsive Pacing," *PACE*, 1986, Part II, vol. 9, pp. 960-964.

Patterson, "Possible technique to measure ventricular volume using electrical impedance measurements with an oesophageal electrode," *Medical & Biological Engineering & Computing*, 1987, 25:677-679.

Plicchi et al., "Monitoring Intrapulmonary Bioelectric Impedance During Active Volume Overloading," *Europace Supplements*, 2002, 3:A39, Abstract No. 54/6.

Van De Water et al., "Monitoring the Chest with Impedance," *Chest*, 1973, 64(5):597-603.

Wang et al., "Feasibility of Predicting CHF Hospitalization Using Pacemaker-Based Impedance Sensor in CHF Patients," *J. Cardiac Failure*, 2002, 8(4, Suppl.):S81, Abstract No. 297.

Wang et al., "Feasibility of Monitoring Thoracic Congestion with Impedance Measured from an ICD Lead System in a Chronic Heart Failure Dog Model," *PACE*, NASPE Abstracts, 2000, Part II, vol. 23, No. 4, p. 612, Abstract No. 237.

Yu et al., "Early Warning of CHF Hospitalization by Intra-Thoracic Impedance Measurement in CHF Patients with Pacemakers," *PACE*, NASPE Abstracts, 2002, Part II, vol. 25, No. 4, p. 527, Abstract No. 19.

Simulation Data—relating to Left and Right Pectoral Can Table:and Plots, Corrected Version Dec. 13, 2002, 2 pgs.

* cited by examiner

MONITORING THORACIC FLUID CHANGES

TECHNICAL FIELD

This document relates to measuring an electrical impedance that is related to a volume of fluid in an internal organ, and for example, to detecting changes in pulmonary edema in patients with implanted medical devices.

BACKGROUND

Pulmonary edema is a serious medical condition in which an excessive amount of fluid accumulates in the lungs. This condition usually results from heart failure. As such, some patients who have these heart conditions may also be prone to fluid accumulation in the lungs, that is, pulmonary edema. Heart failure patients may benefit from having an implantable cardiac rhythm management (CRM) device or an implantable resynchronization therapy device. Such implantable medical devices (IMDs) include, for example, implantable pacemakers, cardiac resynchronization therapy (CRT) devices, and implantable cardioverter-defibrillators, or "ICDs", which may also have pacing functionality.

IMDs are usually implanted under the skin in the chest region, and they are designed to detect and treat irregular cardiac conditions via their attached implanted leads and electrodes. IMDs may sense ventricular tachycardia and/or ventricular fibrillation and deliver an electrical shock or other appropriate therapy in response to detecting such rhythms. They have one or more leads with one or more electrodes positioned in or around the heart to supply electrical stimulation to stabilize the heart rhythm, or to resynchronize ventricular contraction. In some IMDs, the housing of the IMD is conductive and serves as a large "can" electrode.

It is possible to use an IMD to detect changes in the volume of the fluid in the lungs by making an electrical impedance measurement across the lungs using the attached implanted electrodes. The more fluid there is in the lungs, the lower the impedance will be. U.S. patent application Ser. No. 10/303,305, filed on Nov. 25, 2002 by the present inventors, describes one way to measure lung impedance using an IMD to make an electrical impedance measurement between an electrode positioned epicardially over the left ventricular wall and connected to the IMD, and another electrode at the IMD itself. The impedance is measured by applying an electrical stimulus current to the implanted electrodes and measuring the resulting voltage using other implanted electrodes, and then calculating the ratio of voltage to current. This method measures the impedance of the thoracic tissues, including the lungs. The impedance is an indication of the fluid volume in the lungs. This measurement may be repeated over time to detect changes in impedance that indicate changes in lung fluid volume. It is also possible to detect fluid changes in the lungs by making an electrical impedance measurement using only external electrodes attached to the skin. In addition, it is possible to detect the volume of fluid in chambers of the heart by making an electrical impedance measurement using "pill" electrodes, swallowed into the esophagus, and external electrodes attached to the skin.

SUMMARY

Generally, the invention provides for the detection of changes in fluid volume in a thoracic region, such as the lung, by internally injecting a current through the region, detecting an induced voltage on the skin of the patient, and calculating an impedance value. This approach may be referred to as a "hybrid" approach in that it is partially internal and partially external.

In one aspect, the invention features a method for performing a measurement related to a volume of fluid in a region inside a thorax of a body. The method includes injecting an electrical current between first and second internal electrodes that are implanted in the body and that are positioned such that a portion of the injected current flows through at least a portion of the region. The method also includes measuring a voltage between first and second external electrodes attached to an external surface of the skin of the body. The measured voltage is induced by the injected current. The method also includes calculating an impedance by taking the ratio of the measured voltage and the injected current, wherein the calculated impedance is related to the volume of fluid in the region.

In another aspect, the invention features an apparatus for performing a measurement related to a volume of fluid in a region inside a thorax of a body. The apparatus includes a receiver that receives information about an electrical current injected between first and second internal electrodes. These internal electrodes are positioned such that a portion of the injected current flows through at least a portion of the region. The information received by the receiver is telemetered from a device that is implanted in the body and that injects the current between the electrodes. The apparatus also includes an interface that receives a voltage signal detected by first and second external electrodes that are attached to an external surface of the skin of the body. These external electrodes detect a voltage that is induced by the injected current. Finally, the apparatus includes a processing unit that monitors the fluid volume in the region by calculating an impedance from the voltage signal and the received information about the injected current.

Various implementations of the method and apparatus may include one or more of the following. The region may be a lung. In this example, the first internal electrode may be positioned epicardially over the left ventricle of the heart, and the second internal electrode near the upper portion of the left lung. With the internal electrodes in these positions, the first external electrode may be attached to the anterior left shoulder region near the upper part of the lung, and the second external electrode to the central dorsal region. The injection of current between the first and second internal electrodes may be accomplished by applying a voltage between the internal electrodes using an implantable cardiac device, and the housing of the device may serve as the second internal electrode.

In addition to injecting a current between the first and second internal electrodes in the previously discussed positions, the invention may also involve injecting a second electrical current between a third internal electrode and the second internal electrode. The third internal electrode is implanted in the body and positioned such that a portion of the injected current flows through at least a portion of the lung. It further includes measuring a second voltage between a third external electrode attached to the upper right shoulder region and one of the other external electrodes. The second measured voltage may be induced by the second injected electrical current. In a version of this embodiment, the third internal electrode is positioned in the right atrium of the heart. It may also include calculating a second impedance by taking the ratio of the second measured voltage and the second injected current. Where a second impedance is calculated, a weighted average of the first and second calculated impedances may be computed, and two such weighted averages may be compared to detect changes in pulmonary edema.

In another implementation in which the lung is the region of interest, the injection of current is accomplished by applying a voltage between the first and second internal electrodes using an implantable cardiac device, such as, an implantable cardioverter defibrillator, an implantable pacemaker, or an implantable cardiac resynchronization therapy device. The method and apparatus may provide for measuring a lead impedance of the first and second internal electrodes. The method and apparatus may also involve telemetering a voltage applied to inject the current and the measured lead impedance to a device external to the body, in which case they may further involve calculating the injected current by dividing the telemetered voltage by the telemetered lead impedance.

The method and apparatus may be implemented by telemetering information about the injected current to a device external to the body. The implementation may also involve comparing a number of calculated impedances to detect a change in the volume of fluid in the lung, and using those impedance comparisons to detect changes in pulmonary edema.

These general and specific aspects may be implemented using an apparatus, a system, a method, or a computer program, or any combination of apparatus, systems, methods, and computer programs. In addition, other features and advantages will be apparent from the description and drawings, and from the claims.

DESCRIPTION OF DRAWINGS

Like reference symbols in the various drawings indicate like elements.

DETAILED DESCRIPTION

Figure 1:
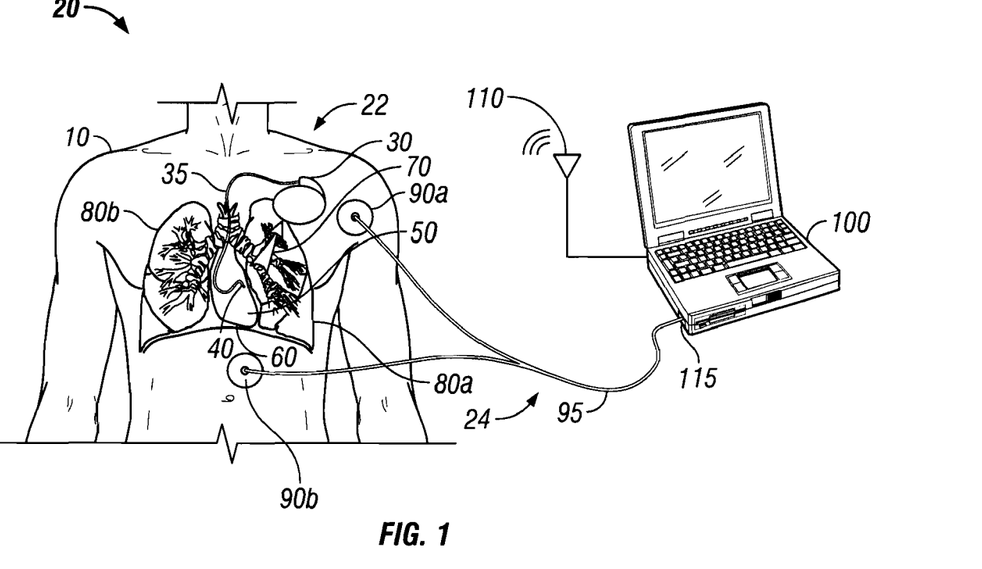
FIG. 1 is a perspective diagram of a system for measuring lung impedance.

FIG. 1 illustrates internal organs in a body 10 and a monitoring system 20 in which an implanted device 22 and an external system 24 cooperate to measure the electrical impedance of an internal organ or region, which in this case is a left lung 80a. In the illustrated example, the implanted device 22 includes a pulse generator 30 and is connected to a lead 35 extending therefrom. The lead 35 has, near a distal end, an electrode 40 that has been positioned epicardially over a left ventricle 50 of the heart 60.

Briefly, in operation, the pulse generator 30 injects an electrical current 70 that flows from the electrode 40, through at least a portion of the left lung 80a, and to the pulse generator 30, a housing of which serves as an electrode. The injected current 70 induces a voltage signal on the skin of the patient. A pair of skin electrodes 90a, 90b are appropriately positioned on the skin of the body 10 to sense the induced voltage. The induced voltage signal relates to the fluid status of the internal organ to be measured, as will be described in more detail later.

A cable 95, which is connected to the skin electrodes 90a, 90b, conducts the sensed voltage signal to a processing unit 100, which receives and processes the voltage signal. The pulse generator 30 measures parameters that allow the calculation of the injected current 70, namely pacing voltage and "lead impedance" (i.e., the impedance into which the pulse generator 30 injects the current, which includes the impedance of tissue as well as that of the lead 35 itself), and telemeters this information to the processing unit 100 via antenna 110. The processing unit 100 then computes the injected current, and divides the skin voltage signal value by the injected current signal value to compute an impedance that characterizes the left lung 80a. Repeating this impedance measurement and computation procedure over time and with the same configuration and positioning of the internal and external electrodes yields a meaningful measure of organ fluid status. Successive organ impedance values can be compared to detect changes in impedance values that may correspond to changes in fluid accumulations within an organ. In this example, the fluid status of the left lung 80a may be measured a number of times. Because the impedance value decreases as fluid volume in the left lung 80a increases, successive impedance values may be compared to detect changes in pulmonary edema.

In more detail, the implanted device 22 includes the pulse generator 30, from which the lead 35 extends and provides a conductive path to the electrode 40. Generally, the pulse generator 30 may be any implantable CRM or resynchronization therapy device, such as a defibrillator, a pacemaker, an ICD, or a combination of these. The pulse generator 30 provides an electrical stimulus that the lead 35 and the electrode 40 deliver through one or more internal organs as the injected current 70. The current 70 returns to the pulse generator 30 through the conductive housing of the pulse generator 30. The housing of the pulse generator 30 may be conductive or partially conductive, in which case it is commonly referred to as a "can electrode," and may serve as an electrode that works in cooperation with the electrode 40. In addition, the pulse generator 30 includes circuitry to measure lead impedance. This value, along with the programmed pacing voltage value, allows the determination of injected current. Alternatively, the pulse generator may include a current measurement capability to measure the current 70 that flows between the electrode 40 and the "can" electrode of the implanted device 22, and hence through the tissues and organs therebetween.

In this example, the pulse generator 30 generates the electrical stimulus required to produce the injected current 70, measures the injected current 70 or the parameters to determine it, and telemeters this information to a processing unit 100. Because at least a portion of the left lung 80a lies between the electrode 40 and the "can electrode" of the implanted device 22, at least a portion of the injected current 70 will flow through the left lung 80a. The capability to inject a current, measure parameters that determine the current signal, and telemeter information about the current exists in numerous currently available implantable devices, such as pacemakers, defibrillators, and ICDs, and is likely to exist in new designs of implantable devices in the future. For example, the pulse generator 30 may be a pacemaker that could first generate the electrical stimulus in the form of a pacing pulse at some benign point in the cardiac cycle, and it could then measure the injected current 70. The magnitude of the injected current may vary across individuals. For example, typical pacemakers or ICDs may inject a current that is between, for example, 2 and 6 milliAmperes (mA). If a custom waveform is used to monitor thoracic impedance, as may be the case with pacemakers that sense minute ventilation, the injected current may be substantially smaller.

Regardless of which type of implantable device is used for the pulse generator 30 to generate the electrical stimulus, the electrical stimulus may be generated using a number of techniques and methods. For example, one known technique is for the pulse generator 30 to generate the electrical stimulus in the form of a high frequency, low magnitude signal applied between the electrode 40 and the conductive housing of the pulse generator 30. Such high frequency and low magnitude signals would not disrupt cardiac or other bodily functions. Whichever type of electrical stimulus is used, the pulse generator 30 applies the stimulus, measures the injected current 70 (or, equivalently, measures lead impedance where the applied voltage stimulus is known) associated with the electrical stimulus, and then it telemeters information about the measured current to the processing unit 100. To measure the injected current 70, the pulse generator 30 may use any of a number of methods, for example, the known method of monitoring the voltage across a series current-sense resistor, or by monitoring the exponential decay of the pacing stimulus waveform resulting from discharging the pacing capacitor into the tissues.

The electrode 40 has an exposed conductive area from which the injected current 70 flows to the return electrode, which, in this example, is the conductive housing of the pulse generator 30. Typically, the lead 35 includes a conductive portion at its distal end that forms the electrode 40, and connects at its proximal end to the pulse generator 30, specifically to a plug-in connector in the pulse generator 30.

The positioning of the electrode 40 and the return electrode is determined by several factors. One factor that determines the position of the electrode 40 is that the electrodes must be positioned such that the organ of interest, in this case a lung, receives the maximum available current density associated with the current 70 as possible. In the exemplary electrode configuration, shown in FIG. 1, the distal end of the lead 35 is positioned such that the electrode 40 is located epicardially over the left ventricle (LV) 50 of the heart 60. In alternative embodiments, the return electrode may be separate from the housing of the pulse generator 30, thereby defining a different path for the current 70, for example, an electrode in the header of the pulse generator, or located on another lead. This would, of course, as would any repositioning of an injection electrode in the monitoring system 20, change the path of the current 70 and thereby change the measured impedance. As such, separating the return electrode from the housing of the pulse generator 30 would also allow for greater flexibility in targeting an organ for which the impedance is to be measured. The exemplary arrangement, shown in FIG. 1, is configured such that a significant fraction of the current 70 flows through at least a portion of the left lung 80*a*. As such, the exemplary configuration targets the left lung 80*a* for organ impedance measurement.

The external system 24 includes the skin electrodes 90*a*, 90*b*, the cable 95, and the processing unit 100. The skin electrodes 90*a*, 90*b* are attached to the patient, and the cable 95 transmits the induced voltage signals detected by these electrodes to the processing unit 100. In addition, the processing unit 100 receives information about the injected current 70 by telemetry from the implanted device 22. From the received induced voltage and injected current information, the processing unit 100 then calculates impedance. As such, the external system 24 cooperates with the implanted device 22 to measure organ fluid status.

In this example, the skin electrodes 90*a*, 90*b* detect a voltage induced on the skin by the injected current 70. The skin electrodes 90*a*, 90*b* are positioned to detect a potential difference (voltage) that relates to the organ fluid status. In other words, for a given injected current 70, the detected voltage at a given pair of electrode locations should be optimally related to the fluid content of the organ(s) or tissues through which the current 70 flows. In the case of targeting the left lung 80*a*, for example, some of the current 70 travels through the thoracic cavity without passing through the left lung 80*a*. In that case, the measured impedance is related to fluid volume in the left lung 80*a*, but is also related to the impedances of other bodily tissues through which the current 70 flows. Simulation studies suggest that the left lung 80*a* may typically contribute about 30% of the measured impedance value in the exemplary configuration of FIG. 1.

The cable 95 may be, for example, a cable of the type commonly used in electrocardiograph (ECG) recordings. Near its distal end, the cable 95 is split to accommodate two or more skin electrodes, which, in this example, includes the skin electrodes 90*a*, 90*b*. At the proximal end, the cable 95 has an interface that may plug into the processing unit 100 through a port 115, which may include a connector for connecting to the interface of the cable 95. When the interface portion of the cable 95 is plugged into the port 115, then the cable 95 conducts voltage signals detected by the skin electrodes 90*a*, 90*b* so that the processing unit 100 receives information about the induced voltage.

FIG. 1 shows an exemplary position of the skin electrodes, with the first skin electrode 90*a* secured in a left-front shoulder region generally to the left of the pulse generator 30. The second skin electrode 90*b* is secured in a central abdominal region generally below and to the right of the electrode 40. In these locations, the skin electrodes 90*a*, 90*b* define a line that is approximately parallel to the line defined by the direct path for the current 70 from the electrode 40 to the housing of the pulse generator 30. In general, what is sought with electrode positioning is to maximize the so-called "dot product" of the current density vector fields of the electrodes. The internal electrodes 40, 30 define a first current density field in the thorax. The skin voltage electrodes 90*a*, 90*b* define a second vector field. In placing the electrodes optimally, one may seek to maximize the vector dot product in the organ of interest by minimizing the angle of intersection between vectors of the current density field and vectors of the second voltage measurement field. Maximizing the magnitudes of those vectors in the organ or region of interest will also maximize the dot product. The current density fields of the injection and voltage measurement electrode pairs depend on the electrode positioning as well as on the internal distribution and properties of tissues. Analysis of these types of fields can be done using computer simulations of the thoracic currents. An example of such analysis is given in Kauppinen P K, Hyttinen J A, Malmivuo J A., *Sensitivity distributions of impedance cardiography using band and spot electrodes analyzed by a three-dimensional computer model. Ann Biomed Eng* 1998;26:694–702. Positions of the skin electrodes other than those shown in FIG. 1 may be equally or more effective for detecting the induced voltage that is related to the fluid content of the organ. For example, the skin electrode 90*b* may be placed on the back of the body in the corresponding locations to detect induced voltage. Computer simulations may be used to study and evaluate the optimal positioning of electrodes.

The processing unit 100, in this example, is a computer-like device with the antenna 110, which may conventionally be a telemetry wand, that communicates wirelessly with the implanted device, for example, to receive telemetered information about the injected current 70. The processing unit 100 also has a port 115 for connecting to the proximal end of the ECG cable 95 to receive information about the induced voltage sensed by the skin electrodes 90a, 90b. From the electrical current information provided by the implanted device 22 and the voltage information provided by the external system 24, the processing unit 100 computes the impedance value using Ohm's law. The computer-like device may be, for example, a special purpose programming device, or "programmer," as is typically supplied by an implantable device vendor for use with that vendor's implantable devices. Such programmer devices may be re-programmed to perform the functions related to organ impedance measurement that are described in this document.

The processing unit 100 computes the impedance value from the received values of voltage and current, although, as will be described below, the processing unit 100 may receive the appropriate values at different times. Because internal organs have electrical resistance, electric field laws predict that the flow of the current 70 will induce a voltage across organs in the body 10, as well as on the surface of the skin. As the fluid content in the organ increases, the resistivity of the organ decreases, and, for a given current, the induced voltage on the skin also decreases. Hence, the thoracic impedance, which is computed by dividing the induced voltage (V, between the skin electrodes 90a and 90b), by the injected thoracic current 70 (I, through the thorax, between electrodes 40 and the can 30) can be determined from $Z=V/I$. The processing unit 100 may then store this result in memory for later recall and purposes of trending, display the result to an operator, or transmit the result to a remote health care provider using, for example, an internet or telephone connection.

In order for the processing unit 100 to compute a meaningful impedance value, the received value of voltage must correspond in time to the received value of the injected current 70. For example, the current and the induced voltage should be measured within minutes of each other, and those related measurements should be received by the processing unit 100 for computing the impedance. This requirement of measurement within a few minutes of each other results from the rate of fluid clearance or accumulation in the lung. This is a relatively slow process, such that current and voltage determination that are separated by a few minutes would be as accurate as those performed in a completely simultaneous manner.

If desired, multiple values may be recorded to verify that the impedance value is consistent. Several successively received values of steady-state voltage and injected current may be used to compute several successive impedance values, which may be averaged to obtain an averaged result.

One method of obtaining coordinated internal current and external voltage measurements would be to first obtain by telemetry the current information, either directly or by its determining elements (lead impedance and pacing voltage). This information is typically obtained during follow-up visits at outpatient clinics. Immediately following such telemetry, and after ensuring that pacing stimulation is occurring by proper programming of the implanted device, the external voltage measurements are taken from the electrodes 90a and 90b, via the cable 95 connected to the port 115.

An alternative method of coordinating the internal current measurement and the external voltage measurement may be commenced by the processing unit 100 sending a command to the implanted device 22 to perform an impedance measurement. The implanted device 22 injects a pulse within a predetermined period of time after the command has been sent, and the induced voltage is then measured by the external device 100 from external electrodes 90a and 90b. Other techniques familiar to one skilled in the art may be used to achieve coordinated values of voltage and current.

In the monitoring system 20, the processing unit 100 receives information about the injected current via telemetry, which allows the implantable device to transmit or receive information wirelessly through the skin. Some commercially available implanted devices 22 can communicate with an external device, commonly referred to as a programmer, which may resemble a laptop computer. These devices may telemeter status information, such as current, voltage, lead impedance, electrogram recordings, activation log, battery condition, etc. to the programmer. The telemetry may employ various wireless techniques such as infrared, ultrasound, magnetic fields, or radio frequency (RF) methods. For example, if the programming unit 100 uses RF to communicate with the implanted device 22, then the antenna 110 may be used to exchange commands or data with the implanted device 22.

In addition to telemetry with a local implanted device 22, some commercially available programmers also support remote communication. This capability permits health care providers to interact with the patient, the implanted device 22, or the programming unit 100 over, for example, phone lines or computer networks. As such, processing units with this capability may improve the ability of patients with implantable devices to receive high-quality health care as outpatients from home.

Figure 2:
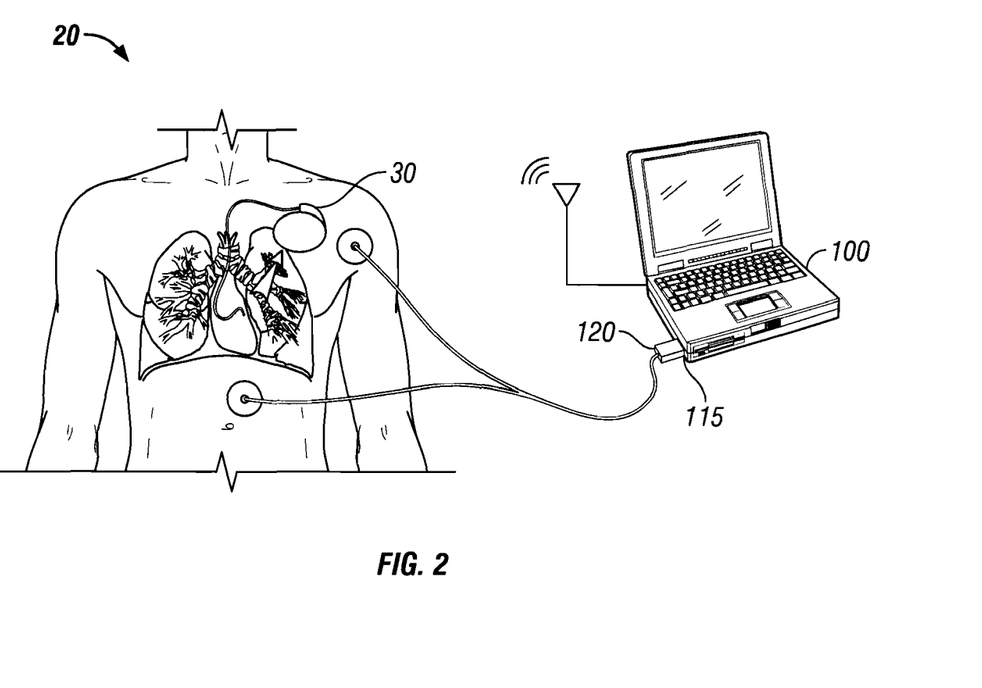
FIG. 2 is the perspective diagram of FIG. 1, with an additional interface element.

FIG. 2 shows the same monitoring system 20 as in FIG. 1, but with the addition of an ECG impedance interface 120. The impedance interface 120 may be necessary in systems in which the processing unit 100 does not have voltage measurement capabilities. Such programmers, as those typically in use today, do not have the requisite voltage input circuitry to interface with the skin electrodes 90a, 90b. The ECG impedance interface 120 provides the appropriate hardware and signal processing functions to convert the induced voltage to a format that may be received and processed by the programmer. The impedance interface 120 may plug in to the programmer through the port 115 (which will be described in more detail later). Alternatively, the impedance interface 120 may provide a visual display (e.g., numeric values) of the detected induced voltage, which an operator could then manually enter into the programmer through a keyboard. The addition of the interface 120 provides a mechanism for using the method described in this document with existing and future programmers that do not have the capability to directly receive the induced voltage information by simply plugging in an ECG cable, as in FIG. 1.

Figure 3:
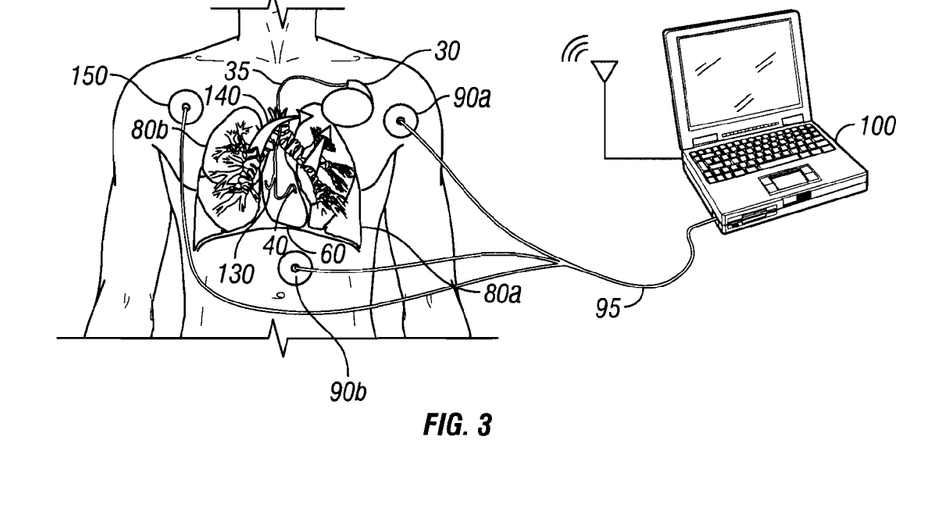
FIG. 3 is the perspective diagram of FIG. 1, with an additional internal electrode and an additional external electrode.

FIG. 3 shows the same monitoring system 20 as in FIG. 1, but where the implanted device 30 has a second lead whose implanted electrode 130 is positioned in the right atrium (RA) of the heart 60. In addition, a third skin electrode 150 is positioned in the right-front shoulder region, generally above and to the right of the electrode 130. In this configuration, it is possible to inject a current 140 through at least a portion of the right lung 80b before returning to the housing of the pulse generator 30. The third skin electrode 150 and either of the skin electrodes 90a, 90b may detect a voltage signal induced on the skin by the current 140, and the cable 95 may transmit that voltage signal to the processing unit 100.

This exemplary configuration of electrodes may be used in several ways. For example, a current 140 may be injected from the right atrium electrode 130 to the "can electrode" of the implanted device 22. An induced voltage may be measured between the skin electrode 150 positioned in the right front shoulder region and the skin electrode 90b positioned, for example, in the central dorsal region. In operation, the monitoring system 20 may make a first measurement by injecting the current 140 and detecting the induced voltage as a measure of the fluid status of the right lung 80b. Then, the monitoring system 20 may make a second measurement by injecting the current 70 and detecting the induced voltage as a measure of the impedance of the left lung 80a.

Computer simulation studies have shown that the right lung may also be monitored with the same internal electrode arrangement described in the preceding paragraph, but with the skin electrode 150 located in the suprasternal notch, just above the sternum. Additionally, the skin electrode 90b may be located in a medial, postero-lateral aspect of the right thorax, over the ribs.

The foregoing describes one method that the system 20 may use to make a number of impedance measurements using the exemplary embodiment shown in FIG. 3. Each of the number of measurements is arrived at by different combinations of internal electrodes that inject current and external electrodes that sense the induced voltage. One way to make a useful measure of lung fluid volume from the resulting number of impedances from each measurement is to assign weights to each impedance and to calculate a weighted average. Different weights may be assigned to each measure, if appropriate, based on known modeling techniques. Such a weighted average may be accomplished either in hardware, by using appropriate resistor networks to implement the weighting, or in software using standard mathematical functions. Using hardware, resistor networks could be incorporated, using methods known from vector-cardiography for example, into the interface circuit 120 shown in FIG. 2. Using software, a weighted combination may be implemented by software running on the processing unit 100.

Figure 4:
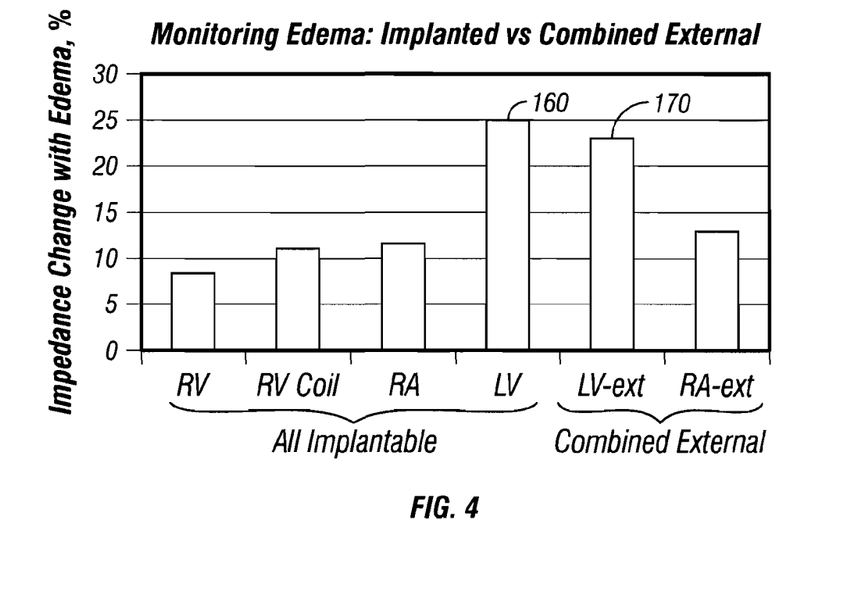
FIG. 4 is a chart comparing the sensitivity of various configurations of all-implantable and combined internal-external edema monitoring systems.

FIG. 4 is a bar chart that compares the sensitivity of four configurations of the all-implanted approach, as described in U.S. patent application Ser. No. 10/303,305, with two configurations of the hybrid approach described in this document. The vertical measure of the bar on the chart indicates the sensitivity for each configuration based on computer simulations performed on human thoracic models. Sensitivity is a measure of the change of impedance resulting from a change in the volume of fluid in an organ.

According to computer simulation studies, the all-implantable LV configuration 160 is the most sensitive because it exhibits the largest percent increase (25%) in measured impedance for a given change in lung fluid volume (edema). The next most sensitive (23%) is the LV configuration 170 using the hybrid approach, and described above with reference to FIG. 1. Thus, computer simulations show that the hybrid approach performs about as well as the all-implantable approach, and can be used with currently-deployed IMDs that lack the capability to measure organ impedance from electrodes such as the LV.

The above-described sensitivity analysis was conducted using a computer model. The model simulates lung impedance under normal and edema conditions using a three-dimensional representation that divided the human thorax into many small volumes, each corresponding to body tissue. Each small volume is assigned a resistivity (e.g. blood=150 ohms-cm, normal lung=1400 ohms-cm, muscle=400 ohm-cm, etc.) according to published tables. Electrodes may then be placed at various locations in the model and current may be injected. The computer then calculates the resulting voltage potentials at each of the volumes using electric field equations. The results can be used to compute impedance by dividing the measured potentials by the injected current.

By observing changes in measured impedance that correspond to changes in lung fluid, physicians may use the monitoring system 20 to look for trends in impedance indicating that the lung fluid is changing over time. The computed impedance need not be an absolute impedance measure to provide a useful diagnostic tool.

It is understood that the measured value of lung impedance may change due to factors that are independent of the volume of lung fluid. For example, the lung impedance value may change if, for example, any of the electrodes, and particularly any of the skin electrodes, change position. Nevertheless, computer simulations show a low sensitivity to small variations in skin electrode positioning in certain regions. This means that the measured impedance value may not change much, for example, in the case of a patient who self-applies the electrodes on an infrequent basis and fails to locate both skin electrodes in exactly the same position each time. Even though the skin electrodes 90a, 90b may be placed in slightly different positions, the monitoring system 20 can still yield organ impedance measurements that may be used to diagnose or monitor pulmonary edema.

Figure 5:
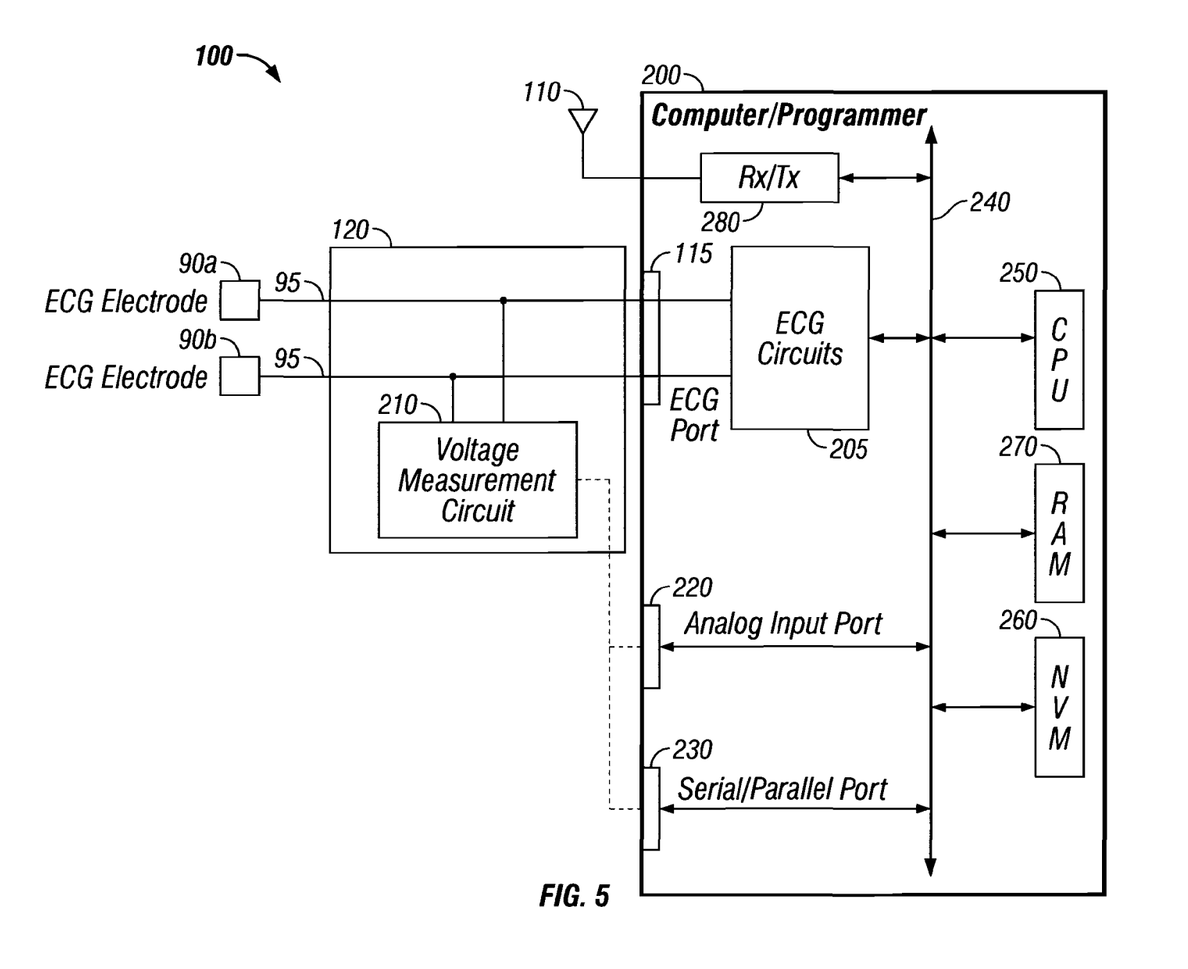
FIG. 5 is a schematic block diagram of a processing unit for use with any of the impedance measuring systems of FIGS. 1–3.

FIG. 5 is a block diagram of the processing unit 100, the interface 120 and the ECG cable 95 of FIG. 1. FIG. 5 shows the impedance computation being accomplished by software running on a computer 200 in the processing unit 100. The ECG interface 120 is plugged into port 115, through which the computer 200 receives inputs from the ECG impedance interface 120. The voltage signals from the skin electrodes 90a, 90b (and possibly 150, not shown) are received in a voltage sensing circuit 210 in the interface 120, which may include filtering, amplification, attenuation, or other appropriate signal processing familiar to one skilled in the art. The circuit 210 may be necessary if, for example, the voltages induced by the stimulation pulse of a pacemaker are so much larger than the normal ECG voltages that they fall outside the dynamic range of an existing ECG circuit 205 in the computer 200. Where this is the case, the existing ECG circuit 205 is not used to determine the lung's fluid status.

Where the existing ECG circuit 205 cannot be used, the circuit 210 in the interface 120 may be used instead to connect to an analog port 220 in the computer 200. The circuit 210 may also include an analog-to-digital converter (ADC) (not shown) to convert the induced voltage measurement to digital format. If digital format is used, the interface 120 may connect to a serial port or a parallel port 230 through which the computer 200 may acquire the voltage measured in the circuit 210.

An alternative solution to the dynamic range limitation of existing ECG circuits is to lengthen the output signal of the circuit 210 so that its duration is visible on a standard ECG display, and to proportionately clamp the output signal provided by the circuit 210 to a value within the dynamic range of the programmer's existing ECG circuit 205. In this way, the pacing voltages may be attenuated, without attenuating the native ECG signals. This allows for both the induced pacing voltages and the ECG to be acquired with the same ECG circuit 205. Because this approach uses existing circuitry, it does not require a separate acquisition path through the analog port 220 or the serial/parallel port 230. The pulse lengthening and proportionate clamping method can be achieved using standard electronic designs known to those skilled in the art.

The computer 200 includes a central processing unit (CPU) 250, a non-volatile memory (NVM) storage unit 260, and a random access memory (RAM) 270, all of which can exchange information over the communication bus 240. The computer 200 also includes a receiver 280 that receives information about the injected current 70 (see FIG. 1) via the antenna 110. The CPU 250 generally includes a microprocessor, and any required supporting circuitry and operating system software, to execute program instructions.

Program instructions may include, for example, code that reads the received voltage or current signal from the receiver/transmitter 280, or code that defines the application program for use with a specific pulse generator 30. Program instructions are typically stored in the NVM 260, which may be located on, for example, hard disk drives, floppy disks, or electrically erasable programmable read-only memory (EEPROM), or their functional equivalents, to provide for retrieval under CPU 250 control. The NVM 260 may store program instructions, such as the application programs for communicating with and controlling the implanted device 30, and it may store data, such as calculated values of organ impedance. In operation, CPU 250 may cause data and program instructions to be copied from the NVM 260 to the RAM 270 over the communication bus 240. In addition, the CPU 250 may communicate with remote computer networks, such as a health service provider's computer network, using known computer telecommunication methods, including the Internet and telephone. Equivalent variations of the just described computer system architecture, which are well known in the art of computer system design, may assembled to execute above-described organ impedance measurement methods on the processing unit 100.

Figure 6:
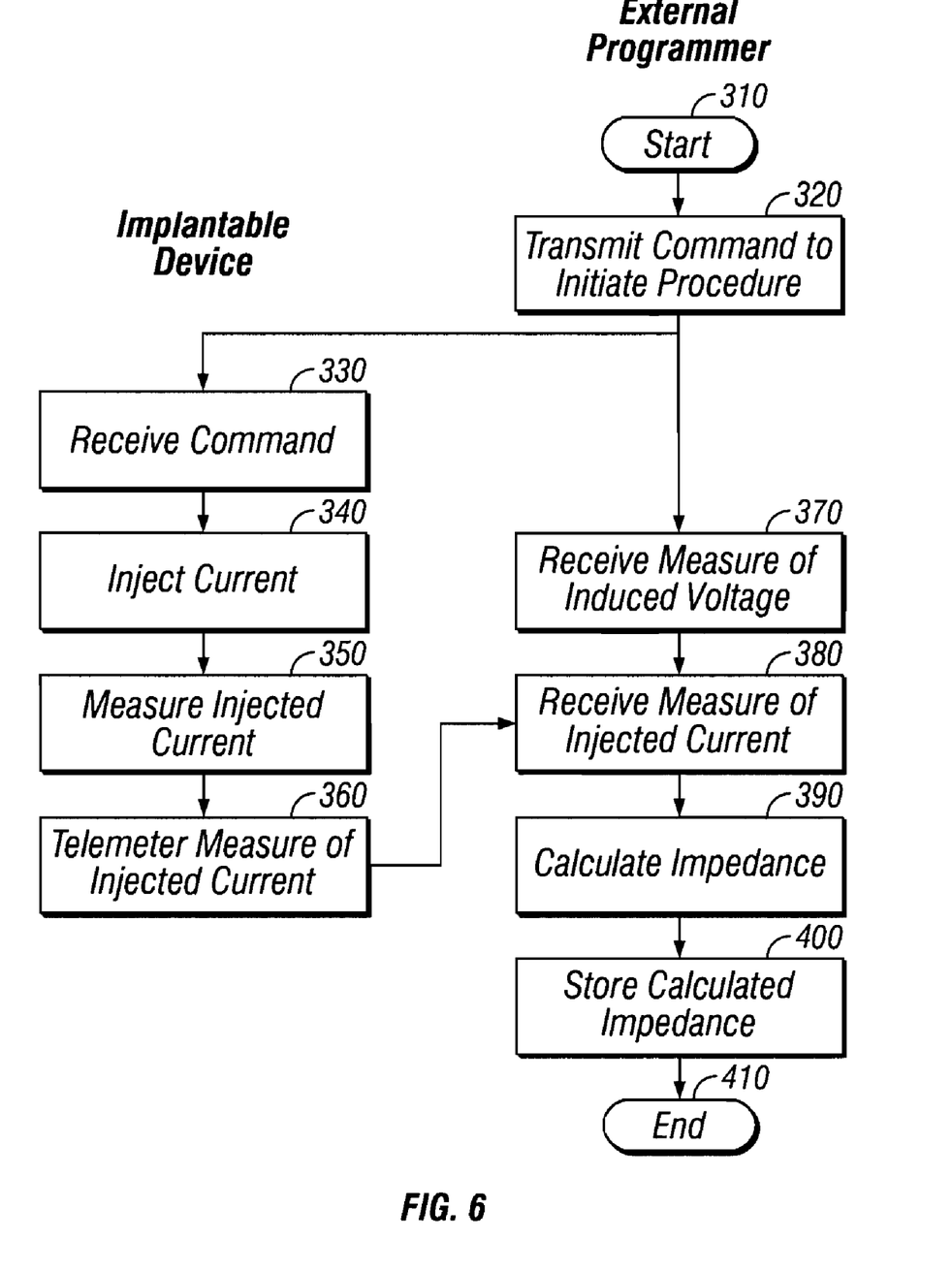
FIG. 6 is a flowchart of the operational steps that may be performed to make an organ impedance measurement.

For one embodiment, FIG. 6 shows a flowchart of the operational steps that may be performed cooperatively by the processing unit 100 (or programmer) and the implantable device 22 to make an organ impedance measurement. The processing unit 100 and the implantable device, in this example, communicate to coordinate the receiving of voltage and current by the processing unit. Each of the steps that are about to be described may be performed in the context of the alternative embodiments described in this document.

The processes starts, at 310, when a user initiates the process by causing the processing unit 100 to execute code programmed to produce an impedance measurement. The processing unit 100 next transmits a command, at 320, to initiate the impedance measurement procedure via the antenna 10 to the implanted device 22. The implanted device 22 receives the command, at 330, and then proceeds to inject the current, at 340, and measure the current, at 350. While the processing unit 100 receives the measured voltage, at 370, through the ECG cable 95, the implanted device telemeters the measured value of the injected current, at 360, which is received by the processing unit 100, at 380, via the antenna 110. The processing unit 100 then calculates the impedance, at 390, from the voltage and current values. Finally, the processing unit 100 stores the calculated impedance, at 400, for later recall, display, transmission, or further processing.

Although FIG. 6 illustrates one embodiment, other embodiments may be used to perform a measurement. For example, pacemakers typically telemeter a lead impedance to a programmer. A physician may fix the pacing voltage, or, if auto-capture is used, the pacemaker may apply a varying voltage. As such, the telemetered pacing voltage value may be a commanded (i.e., not a measured) value that is stored in a memory device in the pacemaker circuitry. If the pacing stimulus may occur regularly and lead impedance and voltage are telemetered out as part of standard patient follow up procedures, then there is no need for a programmer to send a command to initiate the current injection in the manner illustrated in FIG. 6. The programmer may simply continuously acquire the skin voltages, and then may capture a corresponding peak of the induced voltage signal sensed by the skin electrodes 90a, 90b. The programmer can then divide the sensed voltage by the telemetered current value, which the programmer may calculate by dividing the telemetered pacing voltage by the telemetered lead impedance.

Additional Embodiments

In one alternative embodiment, the implanted device 22 does not directly measure the injected current signal (which may be conventionally done with a series current-sense resistor). Instead, the pulse generator 30 may provide either a known or a measured pacing voltage and a measured lead impedance to the processing unit 100. In that case, the pulse generator 30 would telemeter both a pacing voltage value and a lead impedance value, and the processing unit 100 would use the ratio of the pacing voltage to the lead impedance as a substitute for a directly measured current value. The lead impedance value may be telemetered by the IMD 30 as an indication of a broken lead 35.

FIG. 1 shows the lead 35 as unipolar having only one electrode 40; however, a lead can have more than one electrode (e.g., bipolar). In addition, the implanted device 22 may have more than one lead, and each lead may have one or more electrodes disposed at any effective location along the lead.

The implanted electrode(s) may be positioned to inject or receive current in any practical location or position, such as one or more of the following: right ventricle (RV), right atrium (RA), left ventricle (LV), superior vena cava, etc. Various positions and configurations of the electrode 40 may be used to measure the impedance of internal organs in conjunction with the external measurement of the voltage induced by the injected current 70. Multiple electrode arrangements, such as those described in reference to FIG. 3, may be made that include RV electrodes and/or defibrillator electrodes implanted in the heart and superior vena cava.

Moreover, the methods and techniques have been described with reference to measurement of the impedance of the lungs. However, fluid levels in other organs in the body, and in the thorax in particular, may be monitored using the hybrid technique of internal current injection and external induced voltage detection described above in detail with reference to lung impedance. Internal electrodes may be used that are connected to implanted devices that are not necessarily implanted to address a cardiac rhythm problem. The techniques described herein may be used with any implantable medical device that has the requisite pulse generator, current measurement, and telemetry capabilities.

Telemetry of information about the current can be in any technique that is familiar to those in the art. Telemetry methods may include magnetic fields, RF, acoustic energy, optical methods, etc. According to the applied telemetry method, the antenna 110, shown in the exemplary embodiment of FIG. 1, may be replaced by an appropriate wand, infrared receiver/transmitter, transducer, etc. As such, the methods described in this document are not limited to any particular communication link design, so long as the required information can be communicated in a timely manner.

Although only a few embodiments have been described in detail above, those having ordinary skill in the art will certainly understand that many modifications are possible in the preferred embodiment without departing from the teachings thereof. All such modifications are intended to be encompassed within the following claims.

What is claimed is:

1. A method for performing a measurement related to a volume of fluid in a region inside a thorax of a body, comprising:

injecting an electrical current between first and second internal electrodes positioned such that a portion of the injected current flows through at least a portion of the region, the internal electrodes being implanted in the body;

measuring a voltage between first and second external electrodes, the measured voltage being induced by the injected current, the first and second external electrodes being attached to an external surface of the skin of the body; and calculating a first impedance by taking the ratio of the measured voltage and the injected current, wherein the calculated impedance is related to the volume of fluid in the region.

2. The method of claim 1, wherein the region is a lung.

3. The method of claim 2, wherein the injection of current is accomplished by applying a voltage between the first and second internal electrodes using an implantable cardiac device.

4. The method of claim 3, wherein the housing of the implantable cardiac device serves as the second internal electrode.

5. The method of claim 4, wherein the first internal electrode is positioned epicardially over the left ventricle of the heart, and the second internal electrode is positioned near the upper portion of the left lung.

6. The method of claim 5, wherein the first external electrode is attached to the anterior left shoulder region near the upper part of the lung, and the second external electrode is attached to the central dorsal region.

7. The method of claim 4, further comprising:

injecting a second electrical current between a third internal electrode and the second internal electrode, the third internal electrode being implanted in the body and positioned such that a portion of the injected current flows through at least a portion of the lung;

measuring a second voltage between a third external electrode attached to the upper right shoulder region and another of the external electrodes, the second measured voltage being induced by the second injected electrical current.

8. The method of claim 7, wherein the third internal electrode is positioned in the right atrium of the heart.

9. The method of claim 7 further comprising calculating a second impedance by taking the ratio of the second measured voltage and the second injected current.

10. The method of claim 9, further comprising computing a weighted average of the first and second calculated impedances.

11. The method of claim 10, further comprising comparing two weighted averages to detect changes in pulmonary edema.

12. The method of claim 2, further comprising comparing a number of calculated impedances to detect a change in the volume of fluid in the lung.

13. The method of claim 12, further comprising detecting changes in pulmonary edema corresponding to changes in the calculated impedance.

14. The method of claim 1, wherein the injection of current is accomplished by applying a voltage between the first and second internal electrodes using an implantable cardiac device.

15. The method of claim 14, wherein the implantable cardiac device is an implantable cardioverter defibrillator.

16. The method of claim 14, wherein the implantable cardiac device is an implantable pacemaker.

17. The method of claim 14, wherein the implantable cardiac device is an implantable cardiac resynchronization therapy device.

18. The method of claim 14, further comprising measuring a lead impedance of the first and second internal electrodes.

19. The method of claim 18, further comprising telemetering a voltage applied to inject the current and the measured lead impedance to a device external to the body.

20. The method of claim 19, further comprising calculating the injected current by dividing the telemetered voltage by the telemetered lead impedance.

21. The method of claim 1, further comprising telemetering information about the injected current to a device external to the body.

22. An apparatus for performing a measurement related to a volume of fluid in a region inside a thorax of a body, comprising:

a receiver that receives information about an electrical current injected between first and second internal electrodes adapted to be positioned such that a portion of the injected current flows through at least a portion of the region, the received information being telemetered from a device that injects the current, the device and the internal electrodes for being implanted in the body;

an interface that receives a voltage signal detected by first and second external electrodes adapted to be attached to an external surface of the skin of the body, the detected voltage being induced by the injected current; and a processing unit that determines the fluid volume in the region by calculating a first impedance from the voltage signal and the received information about the injected current.

23. The apparatus of claim 22, wherein the region is a lung.

24. The apparatus of claim 23, further comprising an implantable cardiac device that applies a voltage between the first and second internal electrodes to accomplish the current injection.

25. The apparatus of claim 24, wherein a housing of the implantable cardiac device serves as the second internal electrode.

26. The apparatus of claim 25, wherein the first internal electrode is adapted to be positioned epicardially over the left ventricle of the heart, and the second internal electrode is adapted to be positioned near the upper portion of the left lung.

27. The apparatus of claim 26, wherein the first external electrode is adapted to be attached to the anterior left shoulder region of the body, and the second external electrode is adapted to be attached to the central dorsal region of the body.

28. The apparatus of claim 25, wherein the receiver receives information about a second electrical current injected between a third internal electrode and the second internal electrode, the third internal electrode for being implanted in the body and adapted to be positioned such that a portion of the injected current flows through the lung, and wherein the interface receives a second voltage signal detected by a third external electrode and the second external electrode, the third electrode for being attached to the skin in the suprasternal notch region, and the second external electrode for being attached to the postero-lateral region of the right thorax, medially over the ribs.

29. The apparatus of claim 28, wherein the third internal electrode is adapted to be positioned in the right atrium of the heart.

30. The apparatus of claim 28, wherein the processing unit calculates a second impedance by taking the ratio of the second detected voltage and the second injected current.

31. The apparatus of claim 30, wherein the processing unit computes a weighted average of a number of calculated impedances.

32. The apparatus of claim 31, wherein the processing unit compares two weighted averages to detect changes in pulmonary edema.

33. The apparatus of claim 23, wherein the processing unit compares a number of calculated impedances to detect a change in the volume of fluid in the lung.

34. The apparatus of claim 33, wherein the processing unit detects changes in pulmonary edema corresponding to changes in the calculated impedance of the lung.

35. The apparatus of claim 22, further comprising an implantable cardiac device that applies a voltage between the first and second internal electrodes to accomplish the current injection.

36. The apparatus of claim 35, wherein the implantable cardiac device is an implantable pacemaker.

37. The apparatus of claim 35, wherein the implantable cardiac device is an implantable cardioverter-defibrillator.

38. The apparatus of claim 35, wherein the implantable cardiac device is an implantable cardiac resynchronization therapy device.

39. The apparatus of claim 35, wherein the second internal electrode comprises a housing of the implantable cardiac device.

40. The apparatus of claim 35, wherein the implantable medical device measures a lead impedance of the first and second internal electrodes.

41. The apparatus of claim 40, wherein the received information about the injected current further comprises a telemetered value of the voltage applied to accomplish the current injection and a telemetered value of the measured lead impedance.

42. The apparatus of claim 41, wherein the processing unit calculates the injected current by dividing the telemetered voltage value by the telemetered lead impedance value.

43. The apparatus of claim 22, wherein the receiver receives telemetered information about the injected current from an implantable medical device.

* * * * *